United States Patent [19]

Jones et al.

[11] Patent Number: 4,755,389

[45] Date of Patent: Jul. 5, 1988

[54] CHEWABLE CAPSULES

[75] Inventors: Brian E. Jones, Basingstoke; Paula M. Knight, Wolverhampton; Mark A. Walker, Basingstoke, all of England

[73] Assignee: Lilly Industries Limited, London, England

[21] Appl. No.: 905,905

[22] Filed: Sep. 10, 1986

[30] Foreign Application Priority Data

Sep. 11, 1985 [GB] United Kingdom ............... 8522453

[51] Int. Cl.$^4$ .................. A61K 9/52; A61K 7/16; A23G 3/30
[52] U.S. Cl. .................. 424/456; 424/441; 424/485
[58] Field of Search .............. 424/456, 485, 441

[56] References Cited

U.S. PATENT DOCUMENTS

| 3,427,378 | 2/1969 | Henderson et al. | 424/456 X |
| 4,196,189 | 4/1980 | Raaf et al. | 424/456 |
| 4,292,304 | 9/1981 | Barels et al. | 424/456 X |
| 4,428,927 | 1/1984 | Ebert et al. | 424/456 X |
| 4,532,126 | 7/1985 | Ebert et al. | 424/48 |

FOREIGN PATENT DOCUMENTS

| WO85/00516 | 2/1985 | PCT Int'l Appl. . |
| WO85/03439 | 8/1985 | PCT Int'l Appl. . |
| 1298742 | 12/1972 | United Kingdom . |
| 2057847 | 4/1981 | United Kingdom . |

*Primary Examiner*—Naney A. B. Swisher
*Attorney, Agent, or Firm*—Bruce J. Barclay; Leroy Whitaker

[57] ABSTRACT

A hard gelatin capsule is filled with a chewable composition containing an ingredient for buccal absorption or having buccal activity.

14 Claims, No Drawings

CHEWABLE CAPSULES

This invention relates to capsules, and in particular to gelatin capsules and contents thereof.

There are many occasions where it is of benefit to retain an active ingredient in the mouth for a prolonged period. Such is the case, for examples, with antiseptics, sore throat remedies, cold and cough preparations and dental compositions. It is also frequently desirable to administer pharmaceutical compounds by the buccal and sublingual routes when fast action is desired with potent drugs, thus avoiding gut lumen, gut wall or hepatic first pass elimination. It is known to provide such pharmaceutical compounds in unit dosage form as a powder or liquid contained in a soft gelatin capsule which is bitten to release the drug. However, the problem is that the capsule contents are almost immediately lost down the throat before having effect.

One approach to this problem has been to provide soft gelatin capsules in which the gelatin is rendered chewable by the addition of an insoluble masticatory component. However, this does not overcome the problem of swallowing the contents and a large soft gelatin shell remains in the mouth.

The present invention provides a solution to the problem of providing a unit dosage form in which sufficient of the active ingredient can be provided in contact with the fluids of the buccal cavity and in a form which can be retained in the buccal cavity for an effective length of time.

This invention therefore provides a hard gelatin capsule containing a chewable composition which comprises (a) a semi-solid composition comprising an ingredient for buccal absorption or having buccal activity in association with a non-toxic carrier and (b) a masticatory enhancing agent, said chewable composition being liquid at a temperature below 100° C. Preferably the hard gelatin capsule contains a chewable composition which comprises (a) an ingredient for buccal absorption or having buccal activity, (b) a non-toxic semi-solid carrier and (c) a masticatory enhancing agent, said chewable composition being liquid at a temperature below 100° C.

The carrier may consist, for example, of one or more lipid or water soluble materials, e.g polymers, which may be either natural or synthetic or a mixture of one or more such materials. The melting point of the carrier is preferably in the range 36° C.–60° C. Suitable polymers may be selected, for example, from the range of polyethylene glycols (PEGs) having a suitable melting point and hardness, from the Gelucire range of excipients supplied by Gattefosse or from excipients supplied by Dynamit Nobel such as Witepsol and Softesan. Preferably the PEG has a molecular weight in the range 200–10,000, while a more preferred range is 1000–2000. A particularly suitable polymer is that having a molecular weight of 1540.

Other materials may also be used as the carrier, either alone or in combination with the previous carrier system. Such materials include, for example, vegetable and animal oils and fats, which may optionally be hydrogenated; hydrocarbons; fatty alcohols and acids, such as those with from about 12 to about 18 carbon atoms; and esters and salts thereof.

When the active ingredient is a liquid, it is first formed into a semi-solid composition using a solid carrier. Such carrier may be a colloidal carrier, such as, for example, colloidal silicon dioxide, or a cellulose derivative such as, for example, methyl or ethyl cellulose. Other suitable solid carriers will be readily recognised by those skilled in the art.

The agent having buccal activity may be any agent which it is desired to apply to the buccal cavity, having either a local action, as in the case, for example, of dentally active agents or pharmaceutical agents used in the treatment of sore throats, or of conditions causing discomfort to the palate or gums; or it may be intended for absorption through the buccal membrane to provide rapid relief of symptoms such as those occurring in patients suffering from diseases affecting the heart.

In particular, the present invention is particularly useful in administering cardioactive drugs such as, for example, nifedipine, nitroglycerin, isosorbide dinitrate and propanolol. It is also useful in administering analgesic drugs, such as buprenorphine, pentazocine and phenzocine; hormones, such as oxytocin, oestrogens and methyltestosterone; sedative drugs, such as triazolam and flurazepam.

By the use of this invention, it is possible to incorporate up to 95% by weight of an active ingredient into the composition for filling into a hard gelatin capsule shell. A preferred range would be up to 20% by weight of active material for solid active materials.

The composition in the capsule may contain up to 1000 mg of an active ingredient, and typically would contain from 1 microgram to 250 mg.

The compositions used in the invention can be retained in the mouth for significant periods of time, thus allowing the active ingredient to have a maximal effect. When the capsule is introduced into the mouth, it may be bitten or allowed to dissolve in the salivary secretions of the buccal cavity. In either case the capsule shell soon disperses leaving the chewable mass which is retained in the mouth with ease. It may be chewed for rapid dispersion or it may be lodged under the tongue when more prolonged absorption is required. In order that the composition may be retained in the mouth, it is necessary to incorporate into the composition a masticatory agent which may be one or more of a variety of stabilising or suspending agents. Such agents include, for example, gums, including the natural, synthetic and semi-synthetic gums, such as the Xanthan gums, tragacanth gums, acacia gums, guar gum or locust bean gum; cellulose derivatives such as, for example, sodium carboxymethyl cellulose or hydoxypropylmethylcellulose (HPMC); other agents include alginates, gelatin, povidone, pectin, beeswax. A preferred gum is Xanthan gum, referred to in Martindale. Further components of the composition may include gelling agents, flavouring agents and drug adsorption enhancers.

In preparing compositions of the invention, the preferred carrier is selected from the polyethylene glycols. Many pharmaceutical compounds are soluble in PEG, and are subsequently rapidly released when brought into contact with the salivary fluids.

The active ingredient is mixed with the carrier, together with the masticatory enhancing agent and any other desired components, such as gelling or flavouring agents, and the mixture is stirred and heated where necessary to obtain an homogeneous mix. Suitable quantities of the mix are introduced into capsule shells by standard means.

The masticatory agent has the effect of rendering the composition chewable and aiding retention in the buccal cavity for a period sufficient for the active ingredient to take effect or to be absorbed.

It has been discovered that the amount of stabilising or suspending agent required to provide acceptable chewing and retention properties is critical. Up to 25% may be used but in a preferred feature of the invention the composition contains from 2% to 15% by weight of Xanthan Gum, most preferably about 5%.

In order to render the capsules more acceptable for chewing, it is desirable to add a flavouring agent to conceal any taste of the active material or carrier system.

The most preferred flavouring was found to be peppermint, at a level of 0.2%, since it best concealed the flavour of the carrier systems used in the tests. The flavour also tended to diffuse into the capsule, and helped to disguise the gelatin flavour.

Other suitable flavourings include vanilla and orange. When a citrus fruit flavour is used, it is preferred to add citric acid to enhance the flavour.

The invention is more fully illustrated by the following non-limitative examples. The chewable composition for filling into capsules may be prepared by any of the following methods. The basic method of preparation involves liquefaction of the carrier system, followed by mixing with the other excipients. This mix is then filled, while molten, into capsules.

The following systems may be used:

1. The mix is prepared in a beaker over a water bath and is hand-filled into capsules by syringe.
2. The mix is prepared in a beaker on a hot plate and an automatic Hibar pump fills the capsules.
3. An Elanco Rotop 8 capsule filling machine is used in conjunction with an Elanco Model 8 capsule filling machine.
4. The mix is prepared in a stainless steel jacketed vessel and a Harro Hofliger KFM filling machine is used.
5. A Guisti mixing vessel is used for preparation of the mix which is filled into capsules using a Hofliger and Karg GKF 1500L filling machine.

These methods may be used to prepare various sizes of batches of chewable capsules.

| Component | Weight | Capsule size |
|---|---|---|
| EXAMPLE 1 | | |
| Propranolol | 10 mg | #4 |
| Xanthan gum | 10 mg | |
| Peppermint Oil | 0.4 mg | |
| PEG 1540 | 100 mg | |
| | 120.4 mg | |
| EXAMPLE 2 | | |
| Nifedipine | 6 mg | #4 |
| Xanthan gum | 5 mg | |
| Orange Flavour | 0.3 mg | |
| Citric Acid | 0.4 mg | |
| Gelucire 44/14 | 90 mg | |
| | 101.7 mg | |
| EXAMPLE 3 | | |
| Pentazocine | 50 mg | #2 |
| HPMC | 30 mg | |
| Vanilla Flavour | 1 mg | |
| PEG 2000 | 200 mg | |
| | 281 mg | |
| EXAMPLE 4 | | |
| Evening Primrose Oil | 750 mg | #00 |
| Colloidal Silicon Dioxide | 25 mg | |
| Xanthan gum | 25 mg | |
| Peppermint Oil | 2 mg | |
| | 802 mg | |
| -continued | | |
| Component | Weight | Capsule size |
| EXAMPLE 5 | | |
| Thyroxine | 25 mcg | #4 |
| Peppermint Oil | 0.3 mg | |
| Tragacanth gum | 10 mg | |
| PEG 1000 | 140 mg | |
| | 150.3 mg | |
| EXAMPLE 6 | | |
| Acetylsalicylic Acid | 300 mg | #0 |
| Gelucire 35/10 | 300 mg | |
| Lemon Flavour | 1.2 mg | |
| Xanthan gum | 20 mg | |
| | 621.2 mg | |
| EXAMPLE 7 | | |
| Norethisterone | 5 mg | #1 |
| PEG 1000 | 300 mg | |
| HPMC | 15 mg | |
| Liquorice Flavour | 6 mg | |
| | 326 mg | |
| EXAMPLE 8 | | |
| Hyoscine Hydrobromide | 300 mcg | #1 |
| PEG 1540 | 300 mg | |
| Xanthan gum | 15 mg | |
| Cherry Flavour | 3 mg | |
| | 318.3 mg | |

We claim:

1. A hard gelatin capsule containing a chewable composition which comprises (a) a semi-solid composition comprising an ingredient for buccal absorption or having buccal activity in association with a non-toxic carrier and (b) a masticatory enhancing agent, said chewable composition being liquid at a temperature below 100° C.

2. A hard gelatin capsule containing a chewable composition which comprises (a) an ingredient for buccal absorption or having buccal activity, (b) a non-toxic semi-solid carrier and (c) a masticatory enhancing agent, said chewable composition being liquid at a temperature below 100° C.

3. A capsule as claimed in claim 1 or claim 2, wherein the masticatory agent is a stabilizing or suspending agent.

4. A capsule as claimed in claim 3, wherein the masticatory agent is a gum.

5. A capsule as claimed in claim 4, wherein the gum is Xanthan gum.

6. A capsule as claimed in claim 2, wherein the carrier is a polyethylene glycol having a molecular weight in the range 200–10,000.

7. A capsule as claimed in claim 6, wherein the carrier is a polyethylene glycol having a molecular weight in the range 400–4,000.

8. A capsule as claimed in claim 7, wherein the PEG has a molecular weight in the range 1000 to 2000.

9. A capsule as claimed in any one of claims 1 or 2 wherein the composition comprises up to 95% by weight of active ingredient.

10. A capsule as claimed in claim 2, wherein the composition comprises from up to 20% of a solid active ingredient.

11. A capsule as claimed in claims 1 or 2 wherein the active ingredient is a cardioactive drug or an analgesic drug.

12. A capsule as claimed in claim 1 wherein the ingredient for buccal absorption or having buccal activity is a liquid and the carrier is a solid.

13. A capsule as claimed in claim 12 wherein the carrier is colloidal silicon dioxide or a cellulose derivative.

14. A capsule as claimed in claims 1 or 2 additionally containing a flavouring agent.

* * * * *